(12) United States Patent
Tong et al.

(10) Patent No.: US 11,806,955 B2
(45) Date of Patent: Nov. 7, 2023

(54) METHOD FOR TESTING ADDITIVELY MANUFACTURED ORTHOPAEDIC PROSTHETIC COMPONENTS

(71) Applicant: DePuy Ireland Unlimited Company, Ringaskiddy (IE)

(72) Inventors: Weidong Tong, Warsaw, IN (US); Mahdieh Aghazadeh, Warsaw, IN (US); Christopher B. Anderson, Warsaw, IN (US); Christine L. Douglas, Warsaw, IN (US)

(73) Assignee: DEPUY IRELAND UNLIMITED COMPANY

( * ) Notice: Subject to any disclaimer, the term of this patent is extended or adjusted under 35 U.S.C. 154(b) by 23 days.

(21) Appl. No.: 16/801,579

(22) Filed: Feb. 26, 2020

(65) Prior Publication Data

US 2021/0260841 A1 Aug. 26, 2021

(51) Int. Cl.
*B29C 71/00* (2006.01)
*B33Y 40/20* (2020.01)
*B29L 31/00* (2006.01)

(52) U.S. Cl.
CPC .......... *B29C 71/0009* (2013.01); *B33Y 40/20* (2020.01); *B29C 2071/0027* (2013.01); *B29L 2031/7532* (2013.01)

(58) Field of Classification Search
CPC ........ B29C 71/0009; B29C 2071/0027; B29C 64/35; B33Y 40/20; B29L 2031/7532; B22F 1/00; B22F 3/11; B32B 15/01; C21D 1/09; A61L 27/56; A61L 27/06; A61L 27/32; A61L 27/30; A61L 27/54
See application file for complete search history.

(56) References Cited

U.S. PATENT DOCUMENTS

| | | | |
|---|---|---|---|
| 5,641,323 A | 6/1997 | Caldarise | |
| 8,268,099 B2* | 9/2012 | O'Neill | B23K 26/382 |
| | | | 148/525 |
| 8,470,047 B2 | 6/2013 | Hazebrouck et al. | |
| 8,470,525 B2 | 6/2013 | Erbeldinger et al. | |
| 9,658,148 B2 | 5/2017 | Vacca | |
| 9,816,911 B2 | 11/2017 | Chen et al. | |
| 9,952,133 B2 | 4/2018 | Vacca | |
| 2006/0004466 A1 | 1/2006 | Glocker et al. | |
| 2013/0059319 A1 | 3/2013 | Erbeldinger et al. | |

(Continued)

FOREIGN PATENT DOCUMENTS

| | | | | |
|---|---|---|---|---|
| CN | 109701085 A | * | 5/2019 | ............. A61L 27/56 |
| EP | 0836453 A1 | | 4/1998 | |

(Continued)

OTHER PUBLICATIONS

U.S. Appl. No. 16/365,557, filed Mar. 26, 2019, entitled Three-Dimensional Porous Structures for Bone Ingrowth and Methods for Producing.

*Primary Examiner* — Galen H Hauth
*Assistant Examiner* — Shibin Liang
(74) *Attorney, Agent, or Firm* — BakerHostetler

(57) ABSTRACT

A prosthetic orthopaedic component includes a porous three dimensional structure. The porous three dimensional structure includes post-manufacture residual particles that are to be removed. Methods are therefore disclosed for removing the residual particles and analyzing the particles.

20 Claims, 9 Drawing Sheets

(56) References Cited

U.S. PATENT DOCUMENTS

| | | |
|---|---|---|
| 2016/0103056 A1 | 4/2016 | Vacca |
| 2016/0103058 A1 | 4/2016 | Glensbjerg et al. |
| 2016/0290915 A1 | 10/2016 | Chen et al. |
| 2017/0254738 A1 | 9/2017 | Vacca |
| 2021/0221063 A1* | 7/2021 | Crabtree ................ B08B 3/106 |

FOREIGN PATENT DOCUMENTS

| | | |
|---|---|---|
| EP | 1418013 A1 | 5/2004 |
| EP | 2741310 A1 | 6/2014 |
| EP | 3004838 A1 | 4/2016 |
| EP | 3204756 A1 | 8/2017 |
| WO | 96/40002 A1 | 12/1996 |
| WO | 2013/074168 A1 | 5/2013 |
| WO | 2014/191003 A1 | 12/2014 |
| WO | 2015/073911 A1 | 5/2015 |
| WO | 2016/057923 A1 | 4/2016 |
| WO | 2016/120276 A1 | 8/2016 |

\* cited by examiner

METHOD FOR TESTING ADDITIVELY MANUFACTURED ORTHOPAEDIC PROSTHETIC COMPONENTS

TECHNICAL FIELD

The present disclosure relates generally to prosthetic orthopaedic components, and more particularly to such components including an additively manufactured structure.

BACKGROUND

The embodiments disclosed herein are generally directed towards three-dimensional porous structures for bone ingrowth and methods for producing said structures.

The field of rapid prototyping and additive manufacturing has seen many advances over the years, particularly for rapid prototyping of articles such as prototype parts and mold dies. These advances have reduced fabrication cost and time, while increasing accuracy of the finished product, versus conventional machining processes, such as those where materials (e.g., metal) start as a block of material, and are consequently machined down to the finished product.

Examples of modern rapid prototyping/additive manufacturing techniques include sheet lamination, adhesion bonding, laser sintering (or selective laser sintering), laser melting (or selective laser sintering), photopolymerization, droplet deposition, stereolithography, 3D printing, fused deposition modeling, and 3D plotting. Particularly in the areas of selective laser sintering, selective laser melting and 3D printing, the improvement in the production of high density parts has made those techniques useful in designing and accurately producing articles such as highly dense metal parts.

The additive manufacturing field has created orthopaedic prosthetic components that promote mammalian cell growth and regeneration. Current methods and geometries can control the pore size distribution, which exerts a strong influence on the ingrowth behavior of mammalian cells such as bone, and further produce porous structures having unit cell geometries with pore sizes and porosities simultaneously in the range believed to be beneficial for ingrowth while maintaining structural integrity during the manufacturing process (e.g., 3D printing).

SUMMARY

In accordance with one embodiment, a method is provided for removing at least one particle from an additively manufactured orthopaedic prosthetic component. The method includes the step of submerging at least a portion of the additively manufactured orthopaedic prosthetic component in a liquid. The method further includes the step of sonicating at least a portion of the additively manufactured orthopaedic prosthetic component so as to loosen the at least one particle. The method further includes the step of shaking the additively manufactured orthopaedic prosthetic component so as to evacuate the at least one particle from the additively manufactured orthopaedic prosthetic component.

In one aspect, the loosened at least one particle is detached from the orthopaedic prosthetic component but disposed in the orthopaedic prosthetic component. The shaking step may be performed while the at least one particle is submerged in the liquid. The sonicating step occurs at a sonication frequency, and shaking step occurs at a shaking frequency that is less than the sonication frequency. The liquid is polar in one embodiment. In another embodiment, the liquid is nonpolar. In one aspect, the method can include the step of increasing a density of the liquid. In one aspect, the method can include the step of adding a salt to the liquid to increase the density. In another aspect, the method further includes the step of adding a dispersion agent to the liquid.

In one embodiment, the method includes the step of filtering the at least one particle from the fluid. The filtering step causes the liquid to flow through the filtration substrate, and prevents the at least one particle to flow through the filtration substrate during the causing step. The weight of the at least one particle is determined.

In another embodiment, a method is provided for evaluating an orthopaedic prosthetic component. The method for evaluating the orthopaedic prosthetic component can be performed individually, or in combination with any of the steps associated with the method for removing the at least one particle from the orthopaedic prosthetic component. The orthopaedic prosthetic component includes an additively manufactured structure having a at least one residual particle. The method can include the step of obtaining a magnified image of at least a portion of a substrate and at least one particle supported by the substrate. The magnified image is viewed on a display, and the at least one particle is surrounded by at least one boundary line on the image along a respective outer perimeter of the at least one particle. The method further includes the step of determining at least one of 1) a quantity of the at least one particle, 2) a size of the at least one particle, 3) an aspect ratio of the at least one particle, and 4) a weight of the at least one particle. In some embodiments, the method further includes the step of removing the at least one particle from the orthopaedic prosthetic component.

The method can further include the step of placing the substrate under a microscope so as to generate the magnified image.

In one aspect, the method further includes the step of thresholding the image so as to define the at least one boundary line.

In one aspect, the at least one particle comprises a plurality of groups of particles spaced from each other in their respective entireties, and the method further includes the step of identifying a region of interest on the substrate that surrounds all of the particles prior to the surrounding step. The substrate can comprise a filter paper or any other substrate suitable for supporting the particles. In another aspect, the method further includes the step of thresholding the region of interest so as to surround the plurality of particles with respective boundary lines.

In one aspect, the method includes the step of scanning each at least one particle inside each respective at least one boundary line to determine a characteristic of the at least one particle, the at least one characteristic including at least one of 1) a quantity of the at least one particle, 2) a size of the at least one particle, and 3) an aspect ratio of the at least one particle. The method can include the step of comparing the determined characteristic against a predetermined threshold. In one aspect, the method further includes the step of providing illumination to the region of interest prior to the thresholding step. The illumination of the particles on the substrate can be adjusted to within a predetermined illumination range.

The at least one particle may have been evacuated from an orthopaedic prosthetic component or from a plurality of orthopaedic prosthetic components.

BRIEF DESCRIPTION OF THE DRAWINGS

For a more complete understanding of the principles disclosed herein, and the advantages thereof, reference is now made to the following descriptions taken in conjunction with the accompanying drawings, in which.

DETAILED DESCRIPTION

Figure 1:
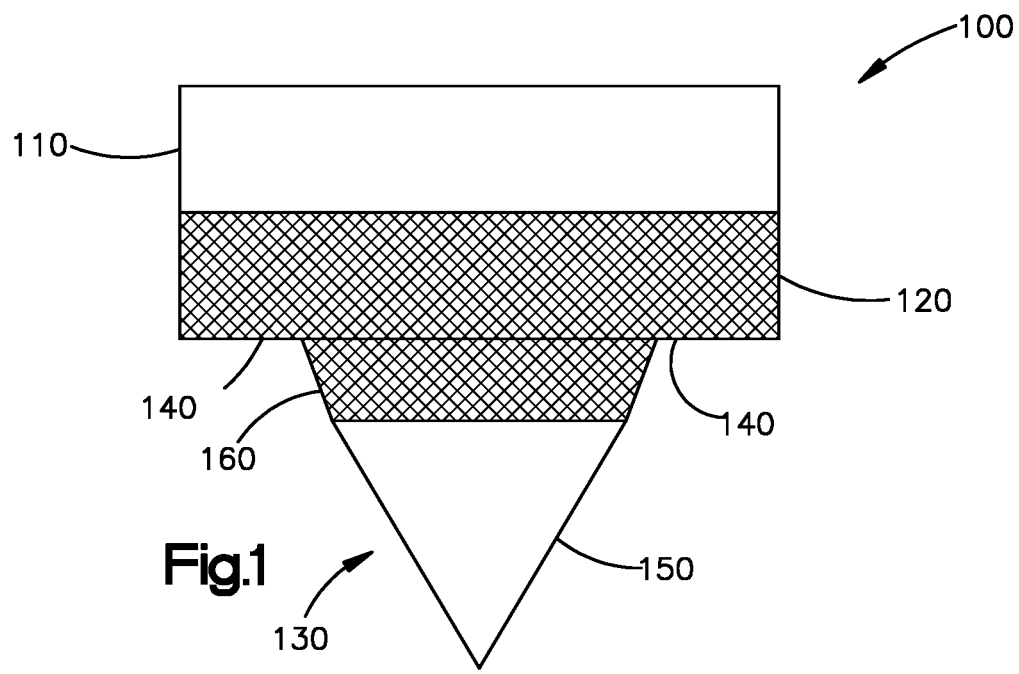
FIG. 1 is a schematic elevation view of an orthopaedic prosthetic component.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims. Further, the term "at least one" stated structure as used herein can refer to either or both of a single one of the stated structure and a plurality of the stated structure. Additionally, reference herein to a singular "a," "an," or "the" applies with equal force and effect to a plurality unless otherwise indicated. Similarly, reference to a plurality herein applies with equal force and effect to the singular "a," "an," or "the."

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Further, references in the specification to "about," "approximately," "substantially," derivatives thereof, and words of similar import, when used to describe one or more parameters including sizes, shapes, spatial relationships, distances, directions, and other similar parameters includes the stated parameter in addition to a range up to 10% more and up to 10% less than the stated parameter, including 5% more and 5% less, including 3% more and 3% less, including 1% more and 1% less.

The present disclosure relates to the additive manufacture of porous three-dimensional metallic structures for orthopaedic prosthetic components, and methods for analyzing the manufacture of such structures. The porous metallic structures promote hard or soft tissue interlocks between prosthetic components implanted in a patient's body and the patient's surrounding hard or soft tissue. For example, when included on an orthopaedic prosthetic component configured to be implanted in a patient's body, the porous three-dimensional metallic structure can be used to provide a porous outer layer of the orthopaedic prosthetic component to form a bone in-growth structure. Alternatively, the porous three-dimensional metallic structure can be used as an implant with the required structural integrity to both fulfill the intended function of the implant and to provide interconnected porosity for tissue interlock (e.g., bone in-growth) with the surrounding tissue. In various embodiments, the types of metals that can be used to form the porous three-dimensional metallic structures can include, but are not limited to, titanium, titanium alloys, stainless steel, cobalt chrome alloys, tantalum or niobium.

Figure 2:
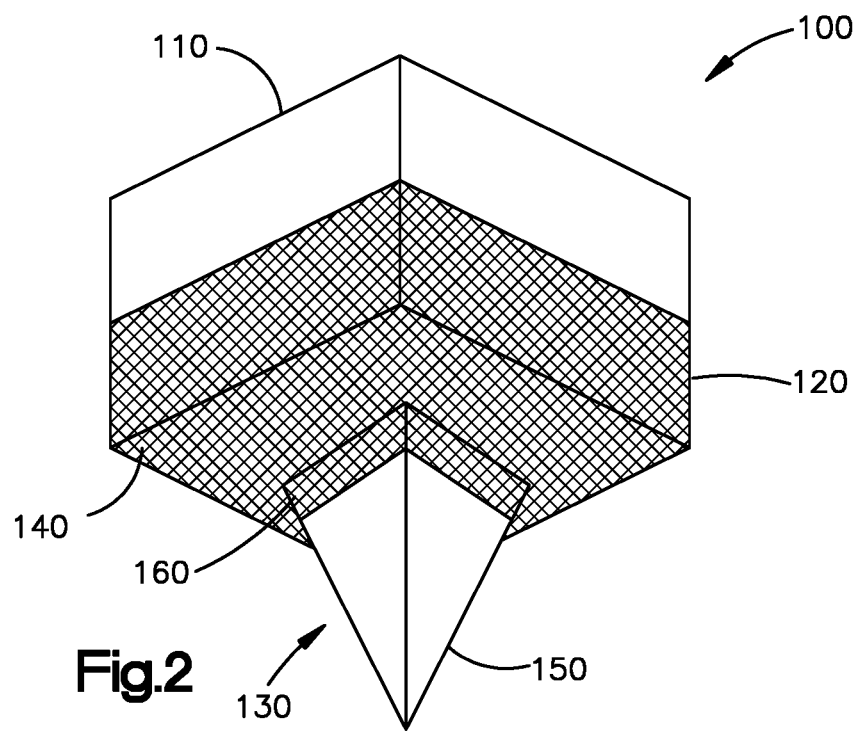
FIG. 2 is a schematic perspective view of the orthopaedic prosthetic component of FIG. 1.

Referring now to FIGS. 1 and 2, an implantable apparatus such as an orthopaedic implant or prosthetic component 100 is illustrated. The prosthetic component 100 includes a base 110, a porous three-dimensional structure or layer 120, and a cone or stem 130 extending away from the base 110. In the illustrative embodiment, the porous structure 120 surrounds a portion of the base 110 and a portion of the stem 130. It should be appreciated that the porous structure 120 can be provided as a layer separate from the base 110 and/or the stem 130. The porous structure 120 may also provide the entire structure of the prosthetic component 100 or as a coating that surrounds some or all of the base 110 and/or all of the stem 130. As described in greater detail below, the porous structure includes a plurality of unit cells that define voids or spaces that permit the ingrowth of bone, thereby promoting fixation of the prosthetic component 100 to a patient's bone.

The orthopaedic implant 100 may be implanted into a tibial bone. For example, the stem 130 can be inserted into the tibial bone, with a ledge portion 140 of implant 100 resting against a proximal portion of the tibial bone. It should be appreciated that the various porous structures described herein may be incorporated into various orthopaedic implant designs, including, for example, a tibial prosthetic component or a femoral prosthetic component similar to the tibial and femoral components shown in U.S. Pat. No. 8,470,047, which is expressly incorporated herein by reference. The porous structures may also be included in other orthopaedic implant designs, including a patella component shaped to engage a femoral prosthetic component and prosthetic components for use in a hip or shoulder arthroplasty surgery It should also be noted, for the preceding and going forward, that the base 110 can be any type of structure capable of, for example, contacting, supporting, connecting to or with, or anchoring to or with components of various embodiments herein. The base 110 can include, for example, a metal or non-metal tray, a metal or non-metal baseplate, a metal or non-metal structure that sits on a tray, and so on. The types of metal that can be used to form the base 110 include, but are not limited to, titanium, titanium alloys, stainless steel, cobalt chrome alloys, tantalum or niobium.

In the illustrative embodiment, the stem 130 includes a solid region 150, which is coated by a porous region 160 of the porous structure 120. The solid region 150 of the stem 130 is anchored to the base 110 and extends outwardly from the porous structure 120 such that the porous structure 120 surrounds the region of stem 130 proximal to base 110. In other embodiments, the stem 130 may be anchored to the porous structure 120. The types of metal that can be used to form the stem 130 include, but are not limited to, titanium, titanium alloys, stainless steel, cobalt chrome alloys, tantalum or niobium.

Figure 3:
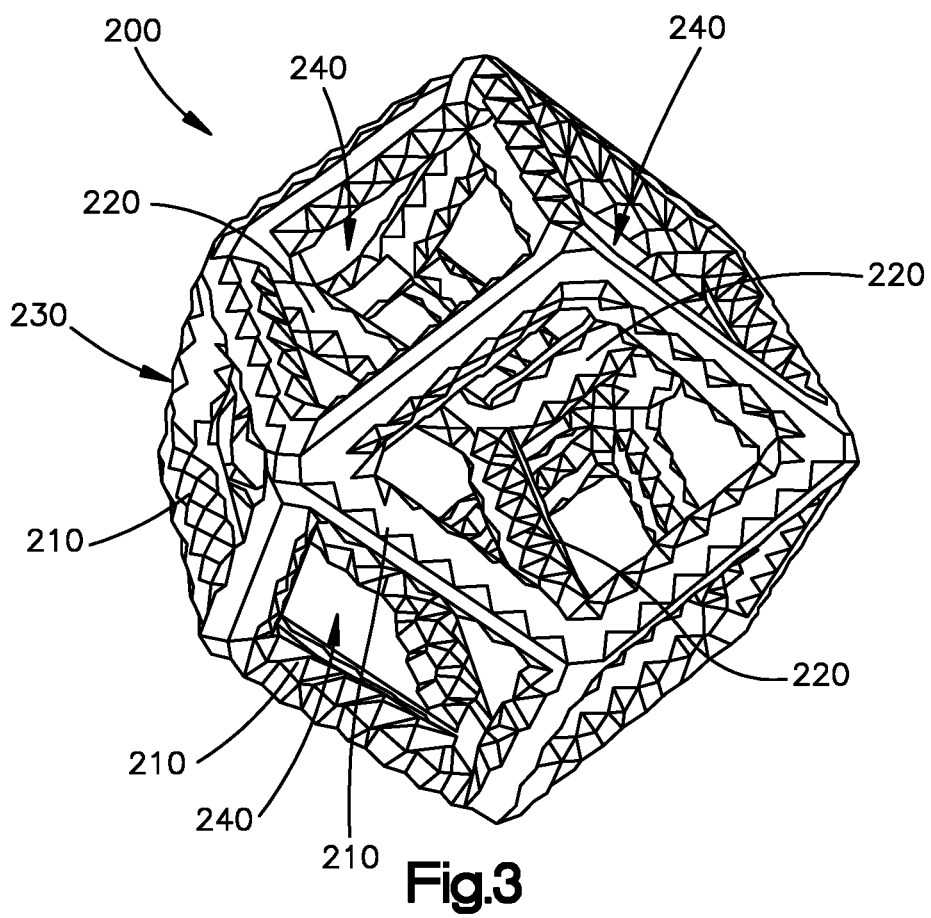
FIG. 3 is a perspective view of a unit cell of the porous structure of the orthopaedic prosthetic component of FIGS. 1-2.

Referring now to FIG. 3, the porous structure 120 of the implant 100 can comprise a plurality of connected unit cells. Each unit cell defines a unit cell structure 200 that includes a plurality of lattice struts 210 so as to define a first geometric structure 230. Each unit cell further defines a plurality of internal struts 220 that are disposed within the first geometric structure 230 so as to define a plurality of second geometric structures 240. In one example, the first geometric structure 230 can include the plurality of lattice struts 210. The lattice struts 210 cooperate to define the first geometry. Each second geometric structure 240 can be formed by a plurality of the internal struts 220 and a plurality of the lattice struts 210. Each of the plurality of second geometric structures 240 can define an internal volume that is substantially equal to the internal volumes of the other second geometric structures 240. In one example, the first geometric structure can be a rhombic dodecahedron, and the second geometric structure can be a rhombic trigonal trapezohedron. It should be appreciated, of course, that the first and second geometric structures can vary as desired. Further, it should be appreciated that the unit cells that make up the casing 33 can have any suitable alternative geometry as desired. For instance, in alternative embodiments, the unit cells can be defined by the plurality of lattice struts 210 without internal struts 220. In other alternative embodiments, the unit cells can be defined by lattice struts 210 and internal struts 220 that define any suitable geometry, respectively, as desired. Examples of such alternative geometries are described in U.S. patent application Ser. No. 16/365,557 filed Mar. 26, 2019, which is expressly incorporated herein by reference.

Figure 4:
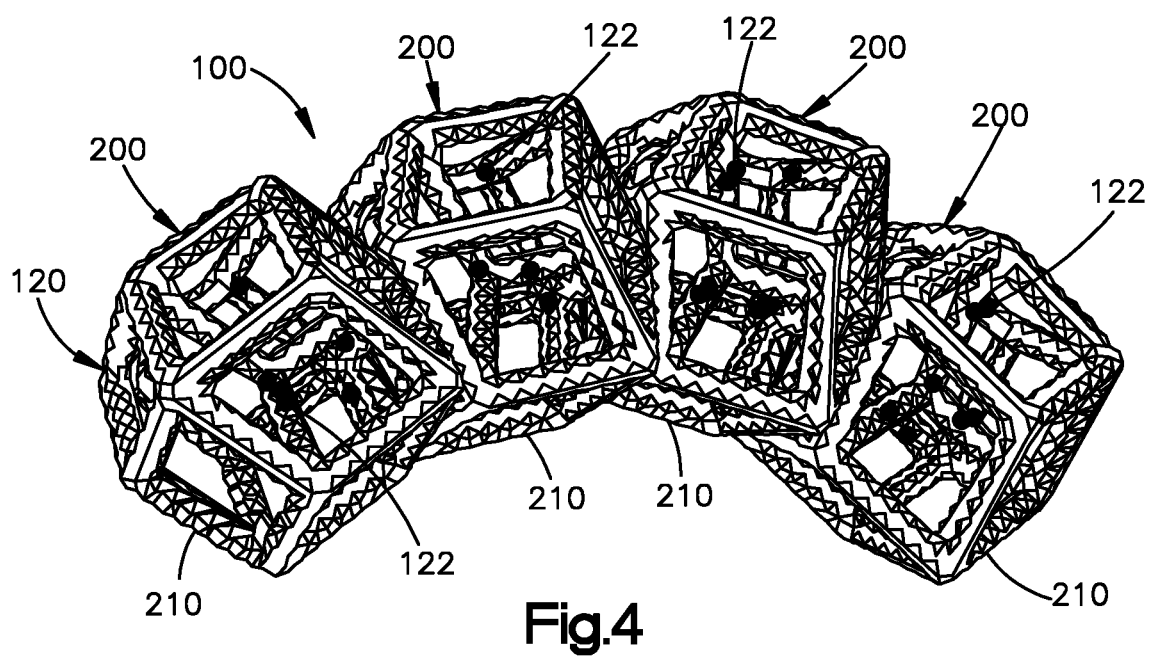
FIG. 4 is an enlarged portion of the orthopaedic prosthetic component illustrated in FIG. 1 as-manufactured, including a plurality of particles to be removed from the orthopaedic prosthetic component.

Referring now to FIG. 4, the porous three-dimensional structure 120 can be fabricated using any suitable additive manufacturing process as desired, including any of the additive manufacturing processes described below. It is recognized that structures created using additive manufacturing processes can include residual particles as artifacts of the additive printing process. For instance, some additive manufacturing processes involve the deposition of a layer of powder onto a base, and fusing the layer of powder to the base. Subsequent layers of powder are deposited onto the respective preceding layers and subsequently fused to the previous layer to form the porous three-dimensional metallic structures. It is recognized that the manufactured porous three-dimensional structure 120 can include quantities of particles 122 that are to be removed prior to use. For instance, the completed part can include residual particles in the form of powder or other particulates. The residual powder can be the product of the additive manufacturing process, and can thus include, but are not limited to, titanium, titanium alloys, stainless steel, cobalt chrome alloys, tantalum or niobium. Alternatively or additionally, the particles can be soil or other debris that may reside on or in the manufactured structure 120.

In order to prevent the orthopaedic prosthetic component 100 from being implanted in a mammalian body while containing these particles 122 that can subsequently become dislodged, it is desirable to remove the particles 122 from the component after the component has been manufactured and prior to implantation. It can be further desirable to analyze the removed particles for quality control purposes, and to ensure that the nature and quantity of the removed particles did not potentially compromise the structural integrity of the additively manufactured porous three-dimensional component.

Figure 5:
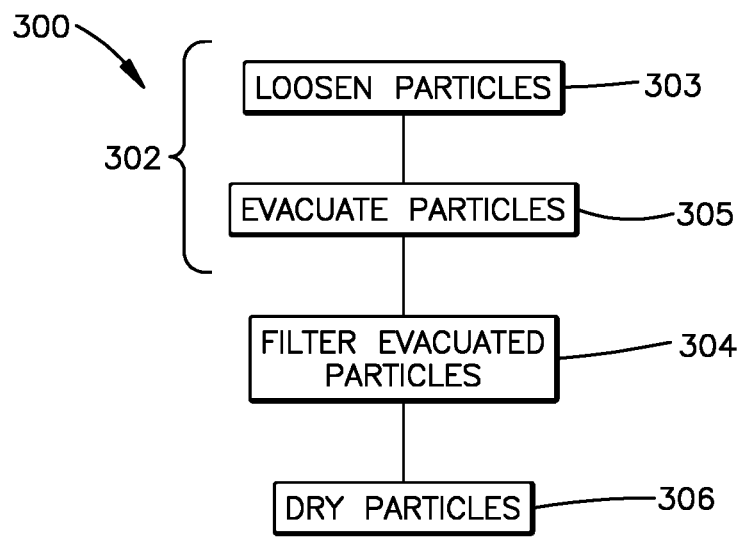
FIG. 5 is a flow chart illustrating steps of one embodiment of a method for removing the particles illustrated in FIG. 4, and preparing the particles for analysis in one example.

Referring to FIGS. 4 and 5, a method 300 is provided for removing the residual particles 122 from the porous three-dimensional structure 120 for subsequent analysis. The method 300 can include the first step 302 of cleaning the prosthetic orthopaedic component 100 so as to remove the particles 122 from the component 100. In some circumstances, the particles 122 can be adhered, bonded, or otherwise attached to the component 100 after the porous three-dimensional structure 120 has been manufactured. For instance, the particles 122 can be adhered, bonded, or otherwise attached to the base 110 and/or the stem 130. Alternatively or additionally, the particles 122 can be adhered, bonded, or otherwise attached to the porous three-dimensional structure 120.

Figure 6:
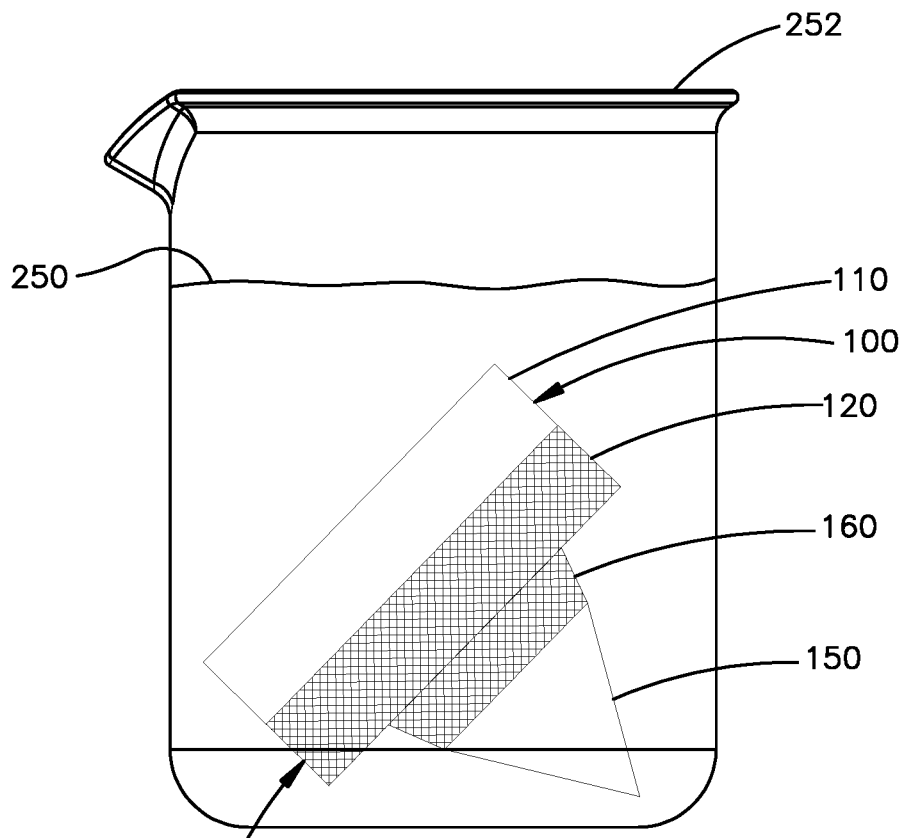
FIG. 6 is a schematic assembly view showing the orthopaedic prosthetic component illustrated in FIG. 4 disposed in a container and submerged in a liquid.

The cleaning step 302 is configured to remove the particles 122 from the component 100. In particular, referring to FIG. 6, at least a portion of the orthopaedic prosthetic component 100 is submerged in a solvent 250 that is disposed in any suitable container 252, such as a beaker or other suitable pourable container. The solvent 250 can be any suitable fluid such as a liquid. In some examples, the liquid can be nonpolar. For instance, the liquid can be water, such as deionized water in some embodiments. Alternatively, the liquid can be substantially polar. For instance, the liquid can be acetone or an alcohol, such as isopropyl alcohol (IPA). Alternatively, the liquid can be oil based. Thus, liquids of different viscosities can be provided. Liquids having high viscosities can increase the transportability of the particles 122 in the solvent 250. The orthopaedic prosthetic component 100 is placed in the container 252 such that at least the porous three-dimensional structure 120 is submerged in the solvent 250. In some embodiments, an entirety of the orthopaedic prosthetic component 100 can be submerged in the solvent 250.

In some embodiments, it is desirable to remove the particles 122 from the component 100 so that the particles can be easily removed from the container 252. Thus, one or more agents can be added to the solvent 250 as desired. For instance, a densifier can be added to the solvent 250 that increases the density of the solvent. In one example, the densifier is salt. Increasing the density of the solvent 250 increases the buoyancy of the particles 122 and reduces the tendency for the particles 122 to accumulate on the bottom of the container 252. Further, increasing the density of the solvent 250 can increase the transportability of the particles 122 in the solvent 250. In some embodiments, it is desirable to prevent or reduce aggregation of the particles 122 in the fluid. Thus, any suitable dispersion agent such as a detergent can be added to the solvent 250 as desired. The dispersing agent increases the dispersion of the particles 122 in the solvent 250. Any one or more of these additives can be included in the solvent 250 as desired.

In some embodiments, for instance when it is desirable to analyze the particles 122 of a single orthopaedic prosthetic component 100, the single orthopaedic prosthetic component 100 is placed in the container 252. In other embodiments, a plurality of orthopaedic prosthetic components 100 can be placed in the container 252. This embodiment can be particularly suitable when it is desired to efficiently analyze the particles 122 of a plurality of orthopaedic prosthetic components 100. This embodiment can also be particularly suitable when it is desired to remove, but not analyze, the particles 122 from a plurality of orthopaedic prosthetic components 100.

Figure 7A:
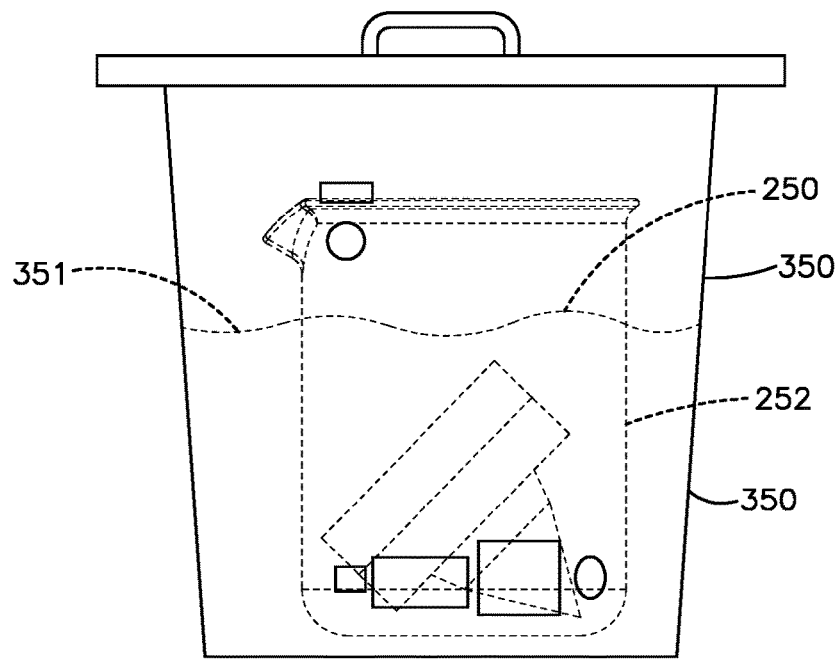
FIG. 7A is a schematic assembly view showing a sonication tank that contains the container illustrated in FIG. 6.

Next, referring to FIG. 7A, the cleaning step 302 includes the step 303 of loosening the attached particles 122 from the prosthetic orthopaedic component 100. In one embodiment, the porous orthopaedic component 100 is sonicated to loosen the attached particles 122 from the prosthetic orthopaedic component 100. In particular, a sonicator 350 may be used to subject the component 100 to high frequency vibration. In the illustrative embodiment, the sonicator 350 is activated to deliver high frequency vibration to the porous orthopaedic component 100. The sonicator 350 can be of the type that includes a sonication tank that contains a sonication liquid 351 configured to deliver the high frequency vibration to the container 252. In some examples the high frequency vibration is delivered to the container 252 at an ultrasonic frequency. The sonication liquid can be water, such as reverse osmosis (RO) water.

The container 252 is placed in the in the sonicator 350 such that the container 252 is disposed in the sonication liquid 351 at a position that prevents the sonication liquid 351 from entering the container 252 during use. The sonicator 350 is activated to deliver high frequency vibration to the container 252 at any suitable sonication frequency for any suitable duration at any suitable temperature. The temperature can be any suitable temperature as desired. In one example, the temperature can be between about 40 degrees F. to approximately 150 degrees F. For instance, the temperature can be room temperature, such as approximately 70 degrees F. The sonication frequency can be within a range from approximately 15 KHz to approximately 400 KHz, or any suitable frequency as desired. In one example, the range of sonication frequencies can be from approximately 25 KHz to approximately 170 KHz. During operation, the sonicator 350 delivers the high frequency vibration to the sonication liquid 351 which, in turn, delivers the high frequency vibration to the container 252 and solvent 250. In particular, the sonication frequency causes cavitation in the solvent 250, which drives the solvent to create forces onto the residual particles that cause the particles to loosen from the prosthetic orthopaedic component 100.

Further, the sonication process can include delivering high frequency vibrations to the container at a plurality of sonication frequencies. For instance, the sonicator 350 can deliver a first high frequency vibration to the container 252 at a first sonication frequency. Next, the sonicator 350 can then deliver a second high frequency vibration to the container 252 at a second sonication frequency. The second sonication frequency can be greater than the first sonication frequency. Next, the sonicator 350 can then deliver a third high frequency vibration to the container 252 at a third sonication frequency. The third sonication frequency can be greater than the second sonication frequency. In one example, the first sonication frequency is one of approximately 25 KHz and 40 KHz. The second sonication frequency is approximately 72 KHz. The third sonication frequency is approximately 104 KHz. The first, second, and third sonication frequencies can be delivered for any suitable time duration as desired. In one example, the time direction can be approximately 10 minutes, though longer or shorter time durations are also envisioned. It is recognized that lower sonication frequencies are more suitable to loosen large particles, and higher sonication frequencies are more suitable to loosen small particles.

Because the orthopaedic prosthetic component 100 is disposed in the container 252 during the sonication process, the residual particles 122 can be easily retrieved from the container 252 if desired. Alternatively, it should be appreciated that the orthopaedic prosthetic component 100 can be placed directly into the sonication liquid 351, and disposed in the sonication liquid 351 during the sonication process.

Figure 7B:
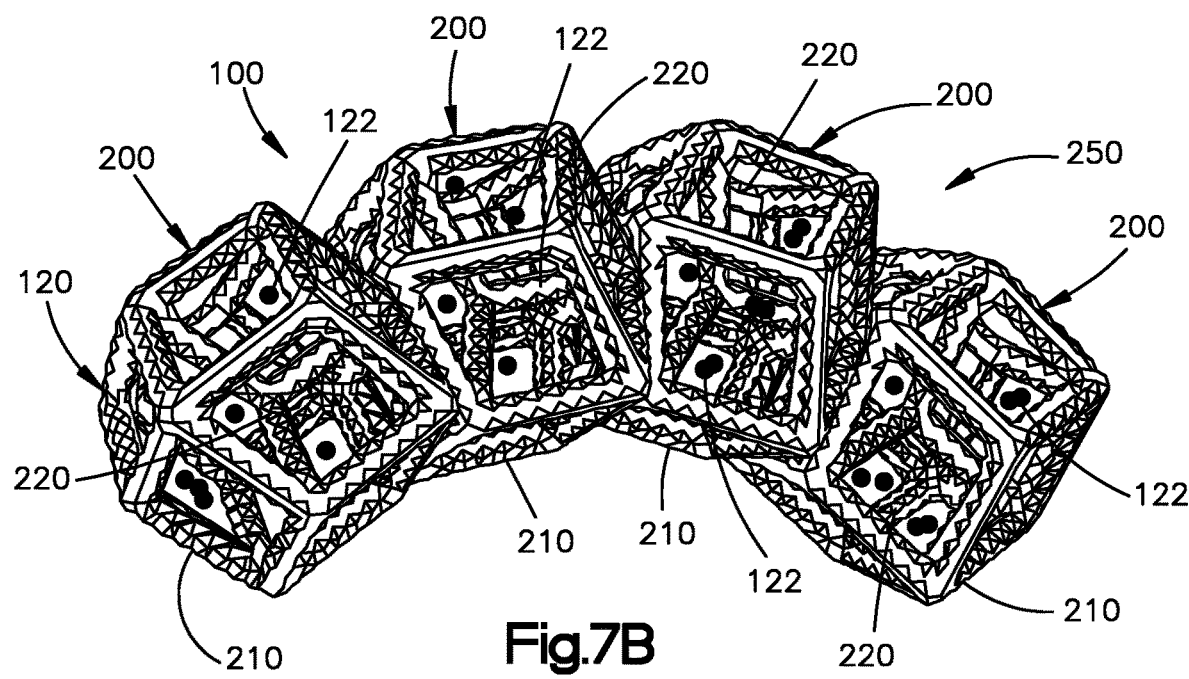
FIG. 7B is enlarged portion of the orthopaedic prosthetic component similar to FIG. 4, but shown after the sonication step of FIG. 7A, whereby the plurality of particles have been loosened from the orthopaedic prosthetic component.

Referring now to FIG. 7B, and as described above, the sonication has caused residual particles 122 that were attached to the prosthetic orthopaedic component 100 to become detached and loosened from the prosthetic orthopaedic component 100. Further, it is recognized that in some examples at least some of the particles 122 can be free from attachment to the prosthetic orthopaedic component 100, but lodged in the component 100, prior to the cleaning step 302. It is appreciated, however, that at least some of the loosened particles 122 may not be evacuated from the orthopaedic prosthetic component 100. For instance, the loosened particles 122 may be trapped in the orthopaedic prosthetic component. In one example, the internal struts 220 and lattice struts 210 can prevent the loosened particles 122 from traveling out of the prosthetic orthopaedic component 100, and in particular out of the porous three-dimensional structure 120.

Figure 8A:
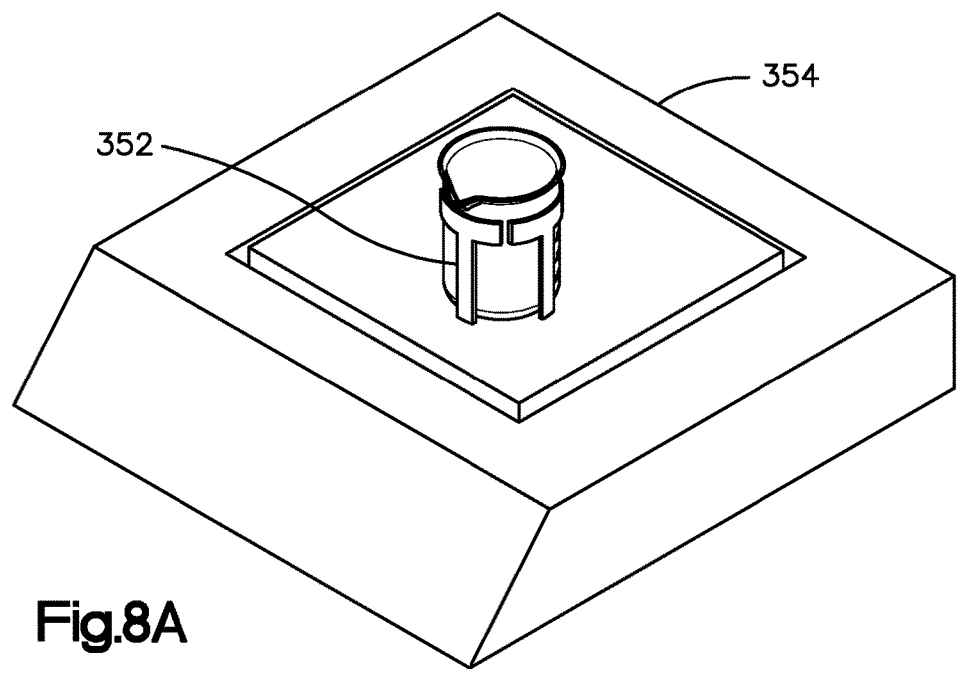
FIG. 8A is a schematic assembly view showing the container of FIG. 6 subjected to a shaking step.
Figure 8B:
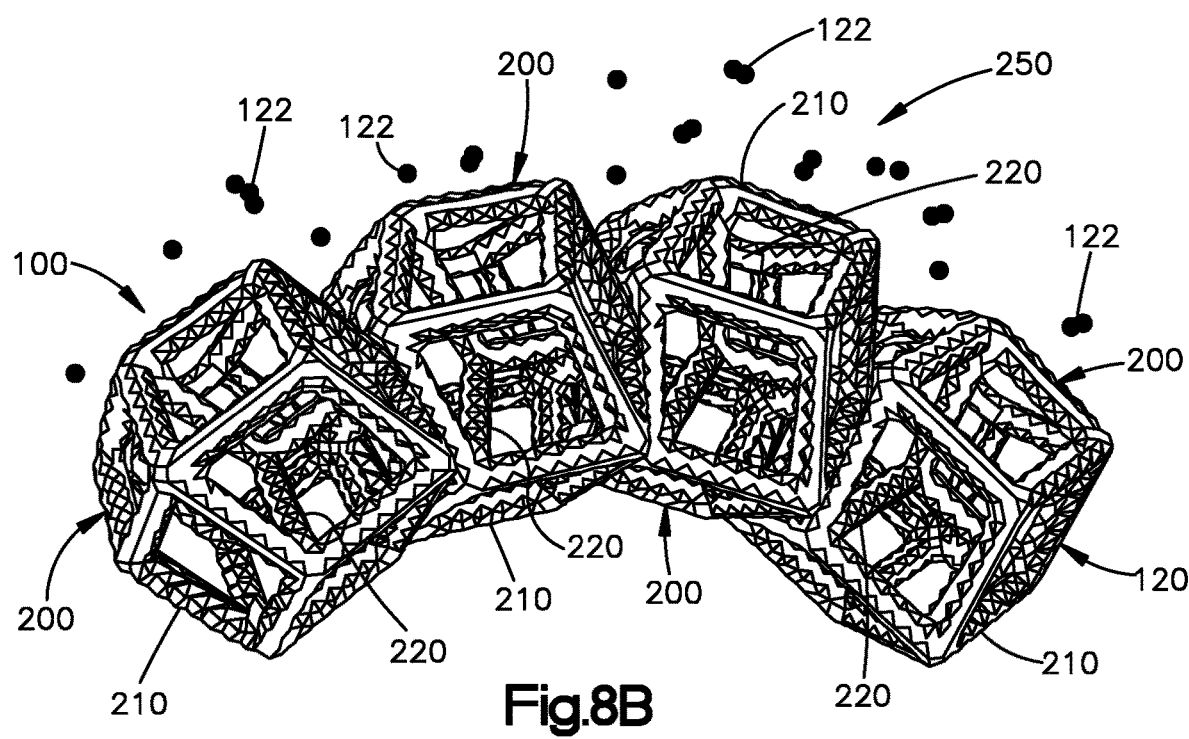
FIG. 8B is enlarged portion of the orthopaedic prosthetic component similar to FIG. 7B, but shown after the shaking step of FIG. 7A, whereby the plurality of particles have been separated from the porous structure.

Accordingly, referring now to FIGS. 5 and 8A, the cleaning step 302 can include a step 305 of evacuating the particle 122 from the orthopaedic prosthetic component 100. The loosened particles 122 may have become loosened during the sonicating step. Alternatively, as noted above, some or all the particles 122 may have been loose from the orthopaedic prosthetic component prior to sonicating. The evacuating step can include the step of shaking the container 252 in order to cause the loose particles 122 to flow out from the prosthetic orthopaedic component 100 in the solvent 250.

The shaking step can include the step of attaching the container 122 to a support member 352 of a shaker apparatus 354. In one embodiment, the container 122 can be placed in the support member 352, such that the support member 352 firmly supports the container 122. Thus, as the support member 352 causes the container 122 to shake, the support member 352 prevents unintended movement of the container 122 during the shaking step. Thus, the shaking step can transport the particles away from the prosthetic orthopaedic component 100. During operation, the shaker apparatus 354 causes the support member 352 to shake the container 122. Shaking of the container 122 causes the solvent 250 to flow inside the container 122, which drives the particles 122 to evacuate the prosthetic orthopaedic component 100. The shaking step can be performed for any duration of time as desired, such as approximately ten minutes in one example. After the shaking step has been completed, the loosened particles 122 that have been evacuated from the prosthetic orthopaedic component 100 are suspended in the solvent 250 in one embodiment. In other embodiments, at least some of the loosened particles 122 can be disposed on the base of the container 122, and subsequently removed from the container 122. The shaking step can cause the container 122 to undergo repeated physical reciprocal motion at a shaking frequency of between approximately 30 and approximately 300 reciprocal (e.g., back and forth) movements per minute, such as between approximately 35 and 100 reciprocal movements per minutes, for instance approximately 60 reciprocal movements per minute. Thus, the shaking frequency is less than the sonication frequency. It is appreciated that the shaking frequency can be adjusted depending on many factors, such as the geometry of the orthopaedic prosthetic component 100 and various characteristics of the particles. During operation, the shaking frequency causes a gentle cavitation in the solvent 250, which creates a flow exchange between the solvent 250 within the orthopaedic prosthetic component 100 and the solvent that surrounds the orthopaedic prosthetic component 100. The solvent 250 within the orthopaedic prosthetic component 100 can contain one or more residual particles 122 that have loosened from the orthopaedic prosthetic component 100 during the sonication step. The flow exchange causes the solvent 250 within the orthopaedic prosthetic component 100, and thus the loosened particles 122 disposed in the solvent 250, to be transported out of the prosthetic orthopaedic component 100.

In this regard, the sonication step can be referred to as a high frequency vibration of the prosthetic orthopaedic component which can be defined by the sonication frequency as described above, and the shaking step can be referred to as a low frequency vibration of the prosthetic orthopaedic component which can be defined by the shaking frequency as described above. The low frequency of vibration is less than the high frequency vibration. For instance, the high frequency vibration can be greater than 500 times the low frequency vibration, for instance greater 1000 times the low frequency vibration. Thus, the method can include the step of subjecting at least a portion of the prosthetic orthopaedic component 100 up to an entirety of the prosthetic orthopaedic component to the high frequency of vibration so as to loosen at least one of the attached particles 122 from the prosthetic orthopaedic component 100, and subsequently subjecting the at least a portion of the prosthetic orthopaedic component 100 up to an entirety of the prosthetic orthopaedic component to the low frequency of vibration so as to evacuate the loosen at least one of the attached particles 122 from the orthopaedic prosthetic component 100.

Referring again to FIG. 5, while the cleaning step 302 can include the sonicating and shaking steps 303 and 305 in one examples, other methods are contemplated for loosening and evacuating the particles 122 from the prosthetic orthopaedic component 100. For instance, a stream of liquid or other vacuum mechanism can be directed at the prosthetic orthopaedic component 100 at a force and for a duration sufficient to loosen and evacuate the particles 122 from the prosthetic orthopaedic component 100. The stream of liquid or vacuum can replace either or both of the sonicating and shaking steps. Of course, it can be desirable to place a container at a location that receives the particles 122 that are removed in response to the stream of liquid. Once the particles 122 have been collected in a suitable container, the method 300 can proceed to step 304 of filtering the particles 122 from the solvent 250.

Figure 9:
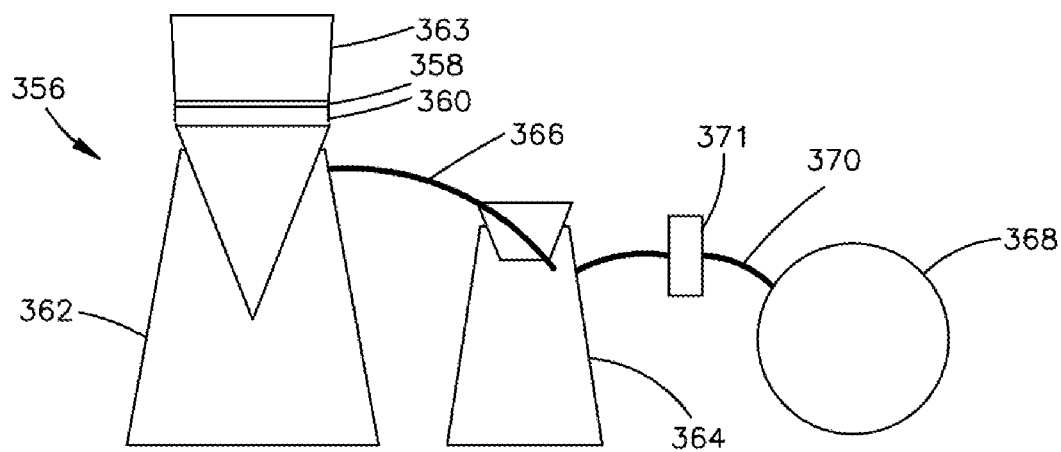
FIG. 9 is a schematic view of a filtration assembly configured to remove the liquid from the particles.

Referring now to FIGS. 7B and 9, a filtration assembly 356 is configured to filter the removed particles 112 from the solvent 250. In particular, the solvent 250 can be driven through a filtration substrate 358, such that the particles 112 accumulate on the substrate 358. The substrate 358 is thus porous with respect to the solvent 250, but nonporous with respect to the particles 112. Further, the filtration assembly 356 can include an air pressure source in the form of an air pump 368 that delivers air pressure to the solvent 250 that drives the solvent through the substrate 358. In one embodiment, the air pressure source 368 is a vacuum that delivers negative pressure to the solvent 250, thereby drawing the solvent 250 through the substrate 358 as the solvent is delivered to the substrate 358. Alternatively, the air pressure source can be a positive air pump that forces the solvent 250 through the substrate 358 as the solvent is delivered to the substrate 358.

Prior to the filtration step, the filtration substrate 358 is weighed. As will be described in more detail below, knowing the weight of the filtration substrate 358 provides for a more accurate subsequent determination of the weight of the particles 112. The filtration assembly 256 further includes a porous support member 360 that is configured to support the filtration substrate 358. In particular, the filtration substrate 358 is placed on top of the porous support member 360. The filtration substrate 358 can further be fastened, such as clamped, to the porous support member 360. The porous support member 360 is porous to air and the solvent 250, such that the solvent that is drawn through the filtration substrate 358 is also drawn through the porous support member 360. In one example, the porous support member 360 can be a screen or mesh. The filtration substrate 358 can be configured as filter paper.

The porous support member 360 can be in fluid communication with a first container 362 that is configured to receive the solvent 250 that passes through the porous support member 360. For instance, the porous support member 360 can be supported directly or indirectly by the first container 362. Further, in one embodiment the filtration assembly 356 includes an inlet 363 that is configured to receive the solvent 250 and particles 122, and directs the solvent 250 to travel through the porous support member 360 and into the first container 362. The filtration assembly 356 can further include a trap container 364 that is in fluid communication with the first container 362. In particular, the filtration assembly 356 includes a drain and a first conduit 366 that extends from the drain of the first container 362 to an inlet of the trap container 364. When the level of liquid in the first container 362 rises to the level of the drain, the liquid in the first container 362 travels along the conduit 366 from the first container 362 to the trap container 364. The inlet of the trap container 364 can be disposed below the outlet of the first container 362.

The filtration assembly 356 further includes an air pump 368 that is in fluid communication with the trap container 364. For instance, the filtration assembly 356 can include a second conduit 370 that extends from the trap container 364 to the air pump 368. The filtration assembly 356 can further include a trap filter 371 disposed in the second conduit 370 that allows air to pass through, but is nonporous with respect to the solvent 250 and water.

During operation, the solvent 250 and particles 122 contained therein are delivered to the inlet 363. The inlet can be configured as a funnel or any suitable container with an open end that receives the liquid and particles 122 disposed in the liquid. Thus, the solvent 250 can be poured from the container 252 (see FIG. 6) into the inlet, such that the solvent 250 and the particles 122 are delivered to filtration substrate 358. If desired, an additional quantity of liquid, sch as deionized water, can be sprayed or squirted against the interior walls of the container 252 and emptied into the inlet 363. Thus, particles 122 that might have still remained on a wall of the container 252 is delivered into the funnel. Because the filtration substrate 358 is not sufficiently porous to allow the particles 122 to pass through, the particles 122 amass on an outer surface of the filtration substrate 358 as the liquid flows through the filtration substrate 358.

The air pump 368 is activated so as to induce a negative pressure that drives the solvent 250 and any additional liquid disposed in the inlet 363 (collectively referred to as liquid) through the filtration substrate 358. In particular, the negative pressure induced by the pump 368 is in fluid communication with the filtration substrate 358 through the first container 362, the first conduit 366, the trap container 364, and the second conduit 370. The particles 122 remain on the filtration substrate 358 as the liquid flows through the filtration substrate 358. The liquid flows from the filtration substrate 358 through the porous support member 360, and into the first container 362. If the liquid rises in the first container 362 to a level equal to the drain of the first container 362, the liquid travels through the conduit 366 into the trap container 364, thereby maintaining a negative pressure differential across the filtration substrate 358 as induced by the air pump 368. Once the liquid has been drained from the inlet 363, additional liquid such as deionized water can be sprayed or squirted to the walls of the funnel in order to ensure that particles 122 that remain on the funnel walls are delivered to the filtration substrate 358. The air pump 368 can be deactivated once substantially all liquid has been removed from the funnel.

Figure 10:
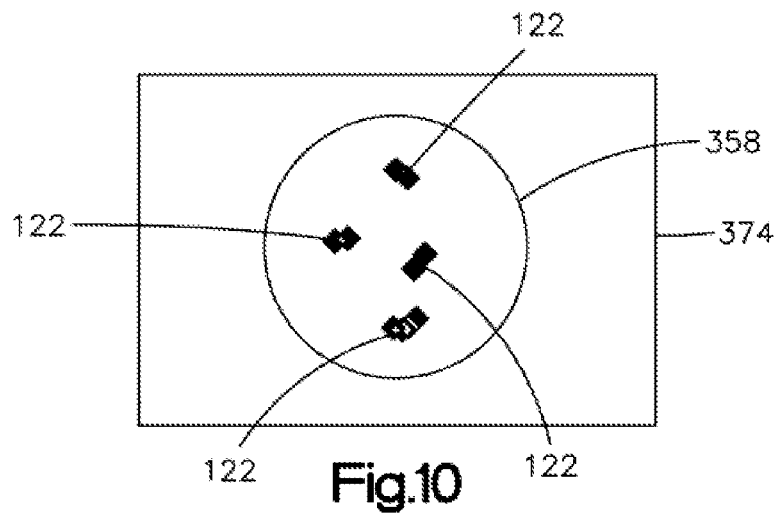
FIG. 10 is a top plan view of a filtration substrate of the filtration assembly of FIG. 9, shown supported on a support structure.
Figure 11:
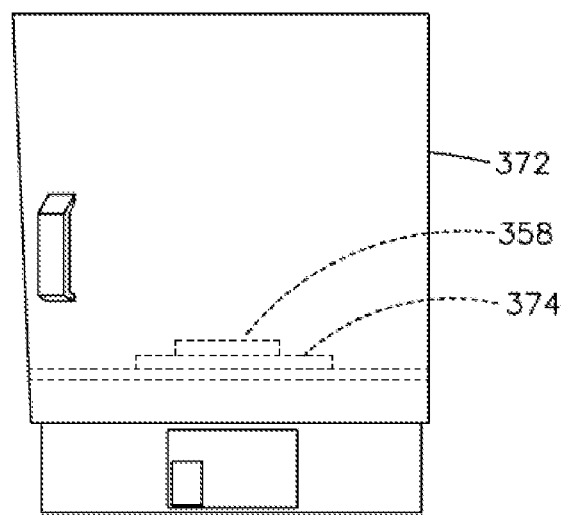
FIG. 11 is a schematic view of the particles disposed in an oven configured to evaporate the liquid.

Next, referring again to FIG. 5, it is recognized that the particles 122 and the filtration substrate 358 are wet after completion of the filtering step 304. Therefore, the particles 122 are dried at step 306. In particular, as illustrated in FIG. 11, the filtration substrate 358 is removed from the filtration assembly and placed into an oven 372 that can heat the filtration substrate 358 to a temperature for a duration of time that is suitable to dry the substrate 358 and the particles 112 disposed on the substrate. In particular, the filtration substrate 358 is removed from the filtration assembly 356 and placed on an optical support member 374. In one embodiment, the support member 374 is configured as an optically transparent support member 374. For instance, as shown on FIG. 10, the optically transparent support member 374 can be a glass slide. As will be described in more detail below, the glass slide 374 is optically transparent that is suitable to allow the particles 122 to be examined under a microscope. The glass slide 374 supports a bottom surface of the filtration substrate 358, while the particles 122 are disposed on a top surface of the filtration substrate 358 that is opposite the bottom surface.

Referring again to FIG. 11, the oven 372 is heated to any temperature suitable for drying the liquid from the filtration substrate 358. For instance, the oven can be heated to any temperature that ranges from approximately 100 degrees F. to approximately 550 degrees F. It can be desirable to heat the oven to a low temperature setting for the purposes of drying the liquid from the filtration substrate 358, particularly when the liquid is water. Accordingly, in one example, the oven can be set to a range from approximately 125 degrees F. to approximately 200 degrees F., such as approximately 150 degrees F. Once the oven 372 has reached the desired temperature, the glass slide 374 and filtration substrate 358 are placed into the oven 372 for a duration suitable to allow the liquid to dry. For instance, the duration of time can be approximately ten minutes or until the filtration substrate 358 and particles 122 have dried.

Figure 12:
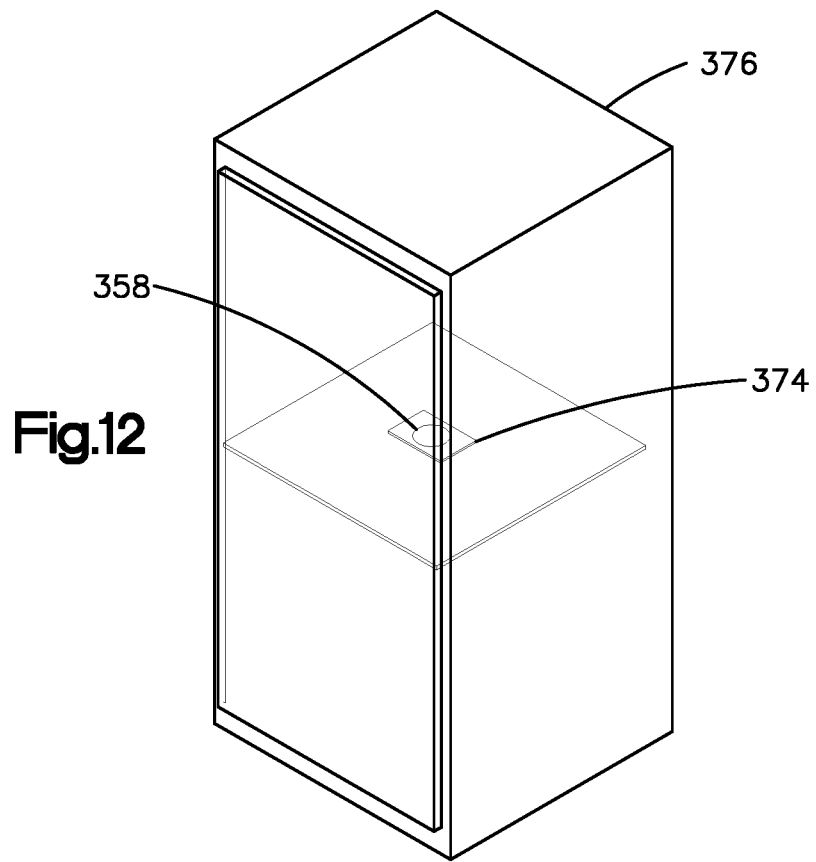
FIG. 12 is a schematic view of the particles disposed in a desiccator configured to decrease a moisture content of the particles.

Next, referring to FIG. 12, the drying step 306 can further include the step of desiccating the filtration substrate 358 and the particles 122. In particular, the glass slide 374 is removed from the oven 372 and placed in a desiccator 376 to remove remaining moisture from the filtration substrate 358 and particles 122. The temperature of the desiccator 376 is brought to room temperature to correspondingly bring the substrate 358 and particles 122 to room temperature and ensure an accurate subsequent weight measurement. Once the glass slide 374 has been removed from the desiccator 376, the filtration substrate 358 is weighed. The difference in weight of the filtration substrate 358 prior to the filtering step 304 and after the drying step 306 provides a filtration substrate 358 weight difference that provides the weight of the particles 122. The weight of the particles 122 can correspond to the particles 122 of a single prosthetic orthopaedic component 100. Alternatively, as described above, a plurality of prosthetic orthopaedic components 100 can be placed in the container 252. Thus, the weight of the particles 122 can correspond to the particles of a plurality of orthopaedic components 100.

Figure 13:
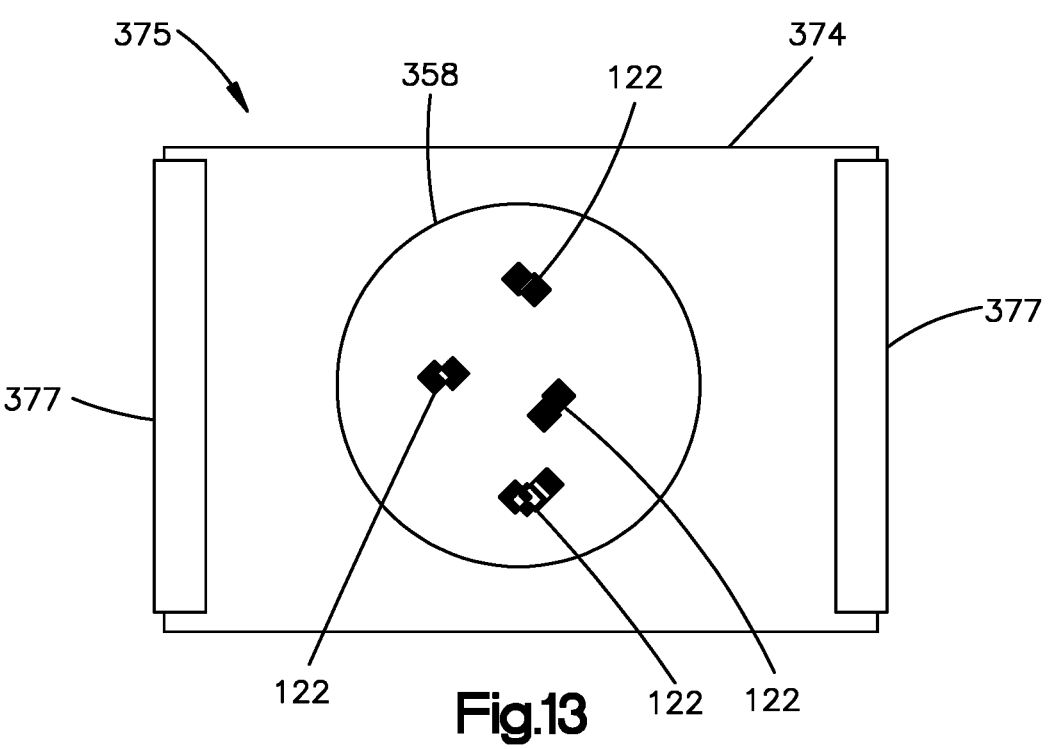
FIG. 13 is a schematic top plan view of the particles disposed on the support structure, wherein the support structure is disposed between two glass slides.
Figure 14:
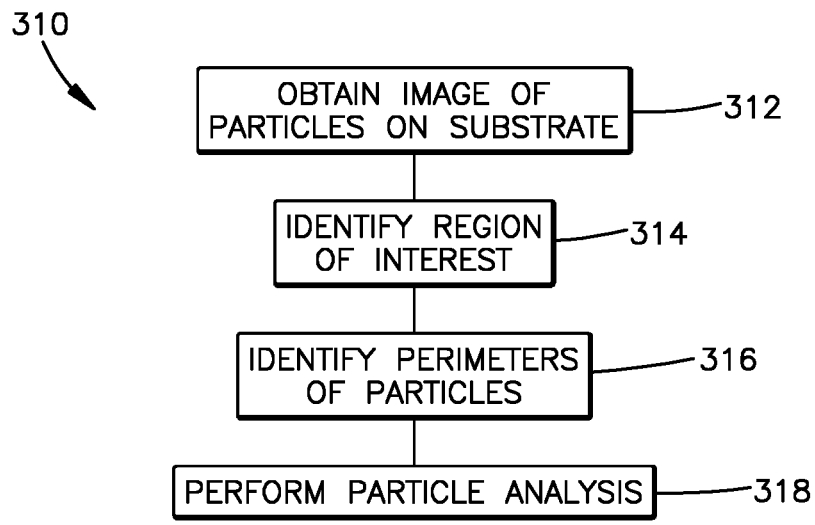
FIG. 14 is a flow chart illustrating steps of one embodiment of a method for analyzing the particles removed from the orthopaedic prosthetic component.

Next, referring to FIG. 14, a method 310 of analyzing the prosthetic orthopaedic component 100, and in particular particles 122 from the prosthetic orthopaedic component 100, can be performed after the method 300 has been completed. The method can determine at least one or more characteristic to all of the characteristics of 1) the quantity of particles 122 disposed on the filtration substrate 358, 2) the sizes of the particles 122, and 3) the aspect ratios of the particles 122. Additionally, the weight of the at least one particle 122 can be determined in the manner described above. As will be appreciated from the description below, the method 300 includes the step of viewing the particles 122 under microscope. Accordingly, as illustrated in FIG. 13, after the filtration substrate 358 supporting the particles 122 has been weighed, the filtration substrate 358 is placed between optically transparent support members 374 so as to define a sample 375, which can be configured as glass slides as described above. Thus, the bottom surface of the filtration substrate 358 is supported by a first glass slide 374, and a second glass slide 374 can cover the top surface of the filtration substrate 358. The second glass slide can be attached to the first glass slide, so that the filtration substrate 358 is captured between the first and second glass slides 374. The first and second glass slides 374 are then attached to each other, for instance using any suitable adhesive 377 such as tape. While it is appreciated that the particles 122 can be disposed on the filtration substrate 358 when placed under the microscope in one example, it should be appreciated that the particles 122 can be transferred from the filtration substrate 358 to any alternative substrate suitable for supporting the particles 122 as desired.

Figure 15:
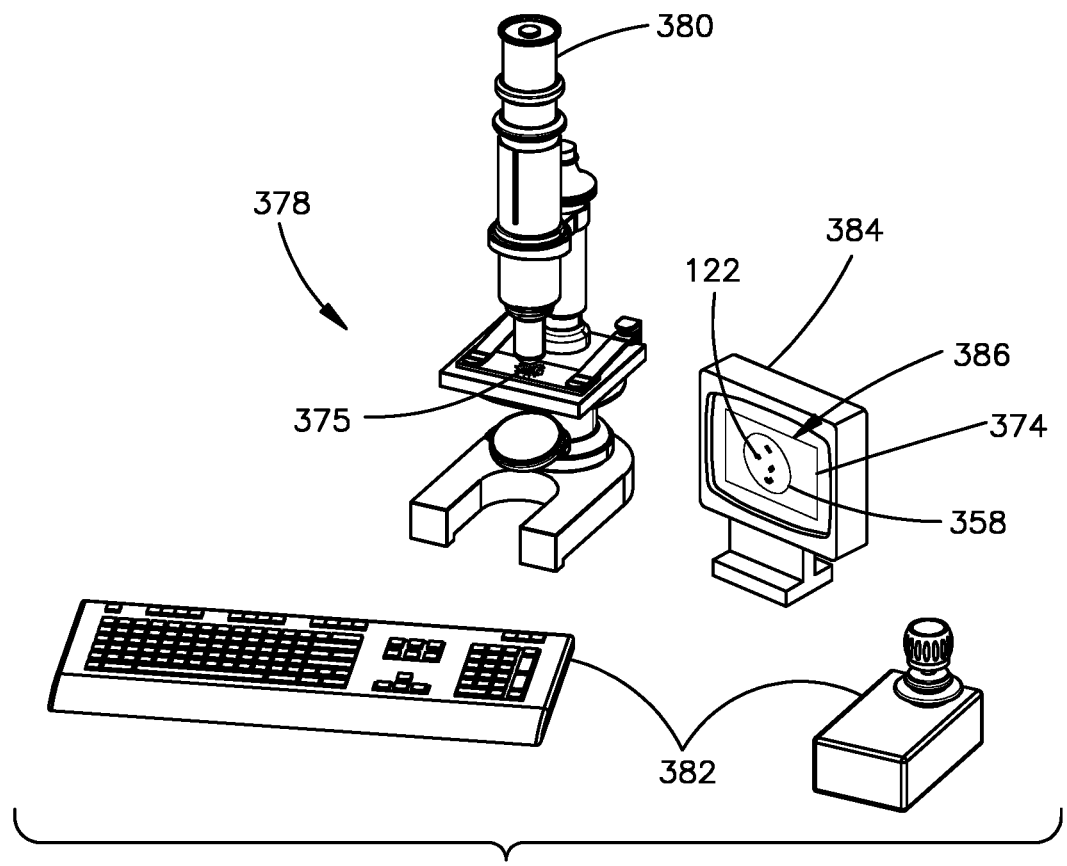
FIG. 15 is a schematic view of a particle analysis station in one embodiment, including a microscope, a display, and an input device, all in communication with a processor operating a stored program to analyze particles placed in the microscope.

As illustrated in FIG. 15, a particle analysis station 378 includes a microscope 380, an input device 382, and a display 384. The input device 382 can be configured as a joystick 383, a keyboard 385, a mouse, any suitable alternative input device, or any desired combination thereof. The particle analysis station 378 further includes a processor that is in data communication with the input device 382 and the display 384. The processor is configured to operates a stored program that is configured to analyze the particles placed under the microscope 380. The stored program can be a Filtrex software program commercially available by Microvision Instruments having a place of business in Evry, France, or any suitable alternative software configured to perform an analysis of the particles as will now be described.

Figure 16:
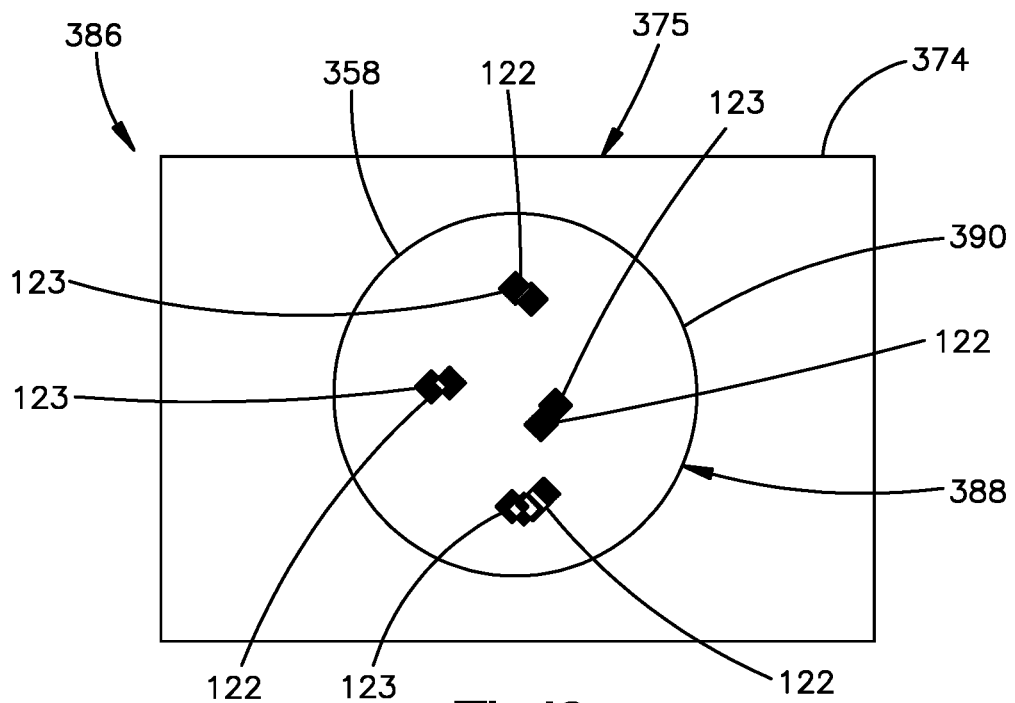
FIG. 16 is a displayed image of the particles disposed on a substrate, further illustrating the step of identifying a region of interest of the substrate.

Referring now to FIGS. 14-16, the method 310 can include the step 312 of obtaining an image 386 of the particles 122 on the filtration substrate 358. In particular, the obtained image 386 can be a magnified image 386 of at least a portion of the filtration substrate 358 and the particles 122 supported on the filtration substrate 358. In some embodiments, it is desirable for the magnified image 386 to include an entirety of the filtration substrate 358 to ensure that the image 386 includes all particles 122 supported by the filtration substrate 358. For instance, the filtration substrate 358 and the particles 122 are placed under the microscope 380. In one example, the sample 375 can be placed under the microscope 380, such that the filtration substrate 358 and the particles 122 are in the field of view. The microscope 380 thus creates the magnified image 386 and outputs the magnified image 386 to the processor, which in turn outputs the magnified image 386 to the display 384.

The microscope 380 has settings that can be adjusted so as to provide a desirable image 386. For instance, the magnification can be set as desired, along with illumination that is applied to the filtration substrate and the particles 122. In one example, the magnification can be set at 5 times or any suitable alternative magnification as desired. Further, it can be desirable to provide substantially uniform illumination to the filtration substrate 358. The substrate 358 and the particles 122 can be illuminated by the microscope 380 under reflected light illumination. In one embodiment, the filtration substrate 358 and the particles 122 can be illuminated by the microscope 380 under reflected light illumination differential interference contrast microscopy (DIC). The particles 122 are brought into focus on the image 386, such that the particles 122 are visually distinguishable from the filtration substrate 358 on the image 386.

The software or other software can receive information regarding the sample 375. For instance, the user can input a unique identified or the sample 375. Further, the user can input the weight change of the filtration substrate 358 as described above, along with the number of prosthetic orthopaedic implants 100 from which the particles 122 supported by the filtration substrate 358 were removed.

Next, referring again to FIGS. 14 and 16, the method 310 can include the step 314 of identifying a region of interest 388 that includes the plurality of particles 122. The region of interest 388 can include all particles 122 that are supported by the filtration substrate 358. The user can input the region of interest 388 on the image 386. The plurality of particles 122 can be arranged in groups 123 of particles that are spaced from each other in their respective entireties. The quantity of groups 123 of particles 122 can be determined as the number of areas defined inside respective boundary lines described above. Alternatively, at least one of the groups 123 of particles 122 can define a single particle 122. In one example, the user can identify the outer perimeter 390 of the filtration substrate 358 as defining the region of interest 388. Alternatively, the user can identify any suitable shape inside the outer perimeter 390 as the region of interest 388. The user can draw a continuous shape that encloses the region of interest 388, or can identify a plurality of points that lie on a continuous shape that defines the region of interest 388. The focus and illumination described above remains applied to the region of interest 388, or can be adjusted if desired to within a predetermined illumination range.

Figure 17:
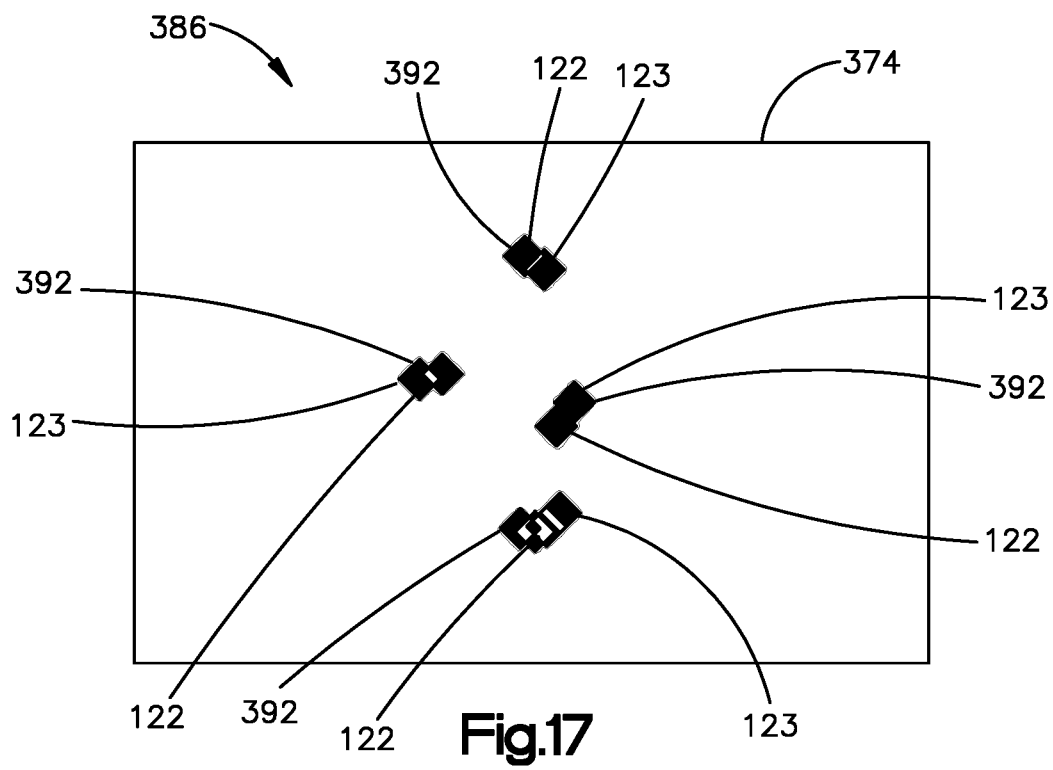
FIG. 17 is a displayed image of the particles shown encapsulated by a boundary line after performing a color thresholding step.

Next, referring to FIGS. 14 and 17, at step 316 a threshold is applied to the image 386 so as to identify an outer perimeter of each of the groups of at least one particle 122. In particular, a color threshold can be applied to the image 386 inside the region of interest 388 so as to surround each of the groups 123 of particles 122 with a respective boundary line 392. In one example, the boundary lines 392 can substantially extend along the outer perimeters of the groups 123 of particles 122, respectively. Accordingly, the software identifies the particles as the area surrounded by the boundary lines 392. Otherwise stated, the area defined inside the boundary lines 392 represent the respective at least one particle 122 or group 123 of particles 122. Analysis on size and shape of the groups 123 of particles 122 can thus be performed based on a corresponding analysis of the area surrounded by the boundary lines 392. In one example, the color threshold can be a gray threshold. In particular, it is recognized that in grayscale, the filtration substrate 358 media has a lighter grayscale hue than the particles 122. Thus, the thresholding can be set to eliminate images lighter than the threshold setting. The software can display a thresholding selection bar that can be adjusted until only the perimeters of the groups 123 of particles 122 are identified. It should be appreciated that while the thresholding is performed in grayscale in one example, the thresholding can be performed for any suitable color as desired based on the color of the particles 122 and the substrate 358 that supports the particles 122. Further, while the thresholding eliminates images lighter than the threshold setting in one example, the thresholding can alternatively eliminate images darker than the threshold setting in other examples, depending on the colors and hues of the particles 122 and the substrate 358.

Referring again to FIG. 14, once the perimeters of the groups 123 of particles 122 have been identified at the thresholding step 316, the method 310 advances to step 318 whereby an analysis of the groups of particles 312 can be performed. In particular, the software can scan the area inside each of the boundary lines 392 generated during the thresholding step 314. In this regard, the software can determine a quantity of the groups 123 of at least one particle 122. Further, the software can measure a size of each of the groups 123 of at least one particle 122. For instance, the software can determine a distance of the perimeters, respectively, of the groups 123. Further, the software can determine respective two perpendicular dimensions of the groups 123 of particles 122, respectively. The dimensions can be oriented along the upper surface of the filtration substrate 358. Further, the dimensions can include a first dimension that extends along a direction of greatest length of the groups 123 of particles 122, respectively. The dimensions can include a second dimension that is substantially perpendicular to the first direction. In this manner, the respective aspect ratio of each of the groups 123 of particles 122 can be determined. Further an area of each of the groups 123 of particles 122 can be measured along the upper surface of the filtration substrate 358. Thus, a cumulative area of all particles 123 can be calculated as the sum of the areas of all of the groups 123 of particles 122.

The method 310 can further include the step of comparing the at least one determined characteristic to a predetermined threshold. If the determined characteristic is greater than the threshold characteristic, the prosthetic orthopaedic component 100 can be discarded. If the determined characteristic is within the threshold characteristic, the prosthetic orthopaedic component 100 can be used as an anatomical implant. For example, if the quantity of determined particles 122 is greater than a predetermined quantity of approved particles 122, the prosthetic orthopaedic component 100 can be deemed unsuitable for implantation. Similarly, if the determined weight of the particles 122 is greater than a predetermined weight, the prosthetic orthopaedic component can be deemed unsuitable for implantation.

Additive Manufacturing Processes

As described above, the porous structure 120 can be manufactured using any suitable additive manufacturing process that involve the use of digital 3D design data to build up a metal component up in layers by depositing successive layers of material. Additive manufacturing processes can include, only by way of example, powder bed fusion printing method (e.g., melting and sintering), cold spray 3D printing, wire feed 3D printing, fused deposition 3D printing, extrusion 3D printing, liquid metal 3D printing, stereolithography 3D printing, binder jetting 3D printing, material jetting 3D printing, and so on.

In various embodiments, a method for producing the porous three-dimensional structure 120 comprises depositing and scanning successive layers of metal powders with a beam to form the porous three-dimensional structure. The beam (or scanning beam) can be an electron beam. The beam (or scanning beam) can be a laser beam. The metal powders can be sintered to form the porous three-dimensional structure. Alternatively, the metal powders can be melted to form the porous three-dimensional structure. The successive layers of metal powders can be deposited onto a solid base (see above for discussion regarding base).

Another method for producing the porous three-dimensional structure 120 comprises applying a stream of metal particles at a predetermined velocity onto a base to form the porous three-dimensional structure. The predetermined velocity can be a critical velocity required for the metal particles to bond upon impacting the base. The critical velocity is greater than 340 m/s in some embodiments. The method can further include applying a laser at a predetermined power setting onto an area of the base where the stream of metal particles is impacting.

Another method for producing the porous three-dimensional structure 120 comprises introducing a continuous feed of metal wire onto a base surface and applying a beam at a predetermined power setting to an area where the metal wire contacts the base surface to form a porous three-dimensional structure comprising a plurality of unit cells and having predetermined geometric properties. The beam (or scanning beam) can be an electron beam. The beam (or scanning beam) can be a laser beam. In various embodiments, the types of metal wire that can be used include, but are not limited to, titanium, titanium alloys, stainless steel, cobalt chrome alloys, tantalum or niobium wire.

Another method for producing the porous three-dimensional structure comprises introducing a continuous feed of a polymer material embedded with metal elements onto a base surface. The method can further comprise applying heat to an area where the polymer material contacts the base surface to form a porous three-dimensional structure comprising a plurality of unit cells and having predetermined geometric properties. In various embodiments, the continuous feed of the polymer material can be supplied through a heated nozzle thus eliminating the need to apply heat to the area where the polymer material contacts the base surface to form the porous three-dimensional structure. The method can further comprise scanning the porous three-dimensional structure with a beam to burn off the polymer material. The beam (or scanning beam) can be an electron beam. The beam (or scanning beam) can be a laser beam.

Another method for producing the porous three-dimensional structure 120 comprises introducing a metal slurry through a nozzle onto a base surface. In various embodiments, the nozzle is heated at a temperature required to bond metallic elements of the metal slurry to the base surface. In various embodiments, the metal slurry is an aqueous suspension containing metal particles along with one or more additives (liquid or solid) to improve the performance of the manufacturing process or the porous three-dimensional structure. In various embodiments, the metal slurry is an organic solvent suspension containing metal particles along with one or more additives (liquid or solid) to improve the performance of the manufacturing process or the porous three-dimensional structure.

Another method for producing the porous three-dimensional structure 120 comprises introducing successive layers of molten metal onto a base surface to form the porous three-dimensional structure. The molten metal can be introduced as a continuous stream onto the base surface. The molten metal can also be introduced as a stream of discrete molten metal droplets onto the base surface.

Another method for producing the porous three-dimensional structure 120 comprises applying and photoactivating successive layers of photosensitive polymer embedded with metal elements onto a base surface.

Another method for producing the porous three-dimensional structure comprises depositing and binding successive layers of metal powders with a binder material to form a porous three-dimensional structure comprising a plurality of unit cells and having predetermined geometric properties. The method can further include sintering the bound metal powder with a beam. The beam (or scanning beam) can be an electron beam. The beam (or scanning beam) can be a laser beam. The method can further include melting the bound metal powder with a beam. The beam (or scanning beam) can be an electron beam. The beam (or scanning beam) can be a laser beam.

Another method for producing the porous three-dimensional structure 120 comprises depositing droplets of a metal material onto a base surface, and applying heat to an area where the metal material contacts the base surface. The heat can be applied using a beam (or scanning beam) that can be an electron beam. The beam (or scanning beam) can be a laser beam. The deposited droplets of metal material can be a metal slurry embedded with metallic elements. The metal material can be a metal powder.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

What is claimed is:

1. A method for removing a plurality of particles from an additively manufactured orthopaedic prosthetic component, the method comprising the steps of:
    submersing at least a portion of the additively manufactured orthopaedic prosthetic component in a liquid;
    sonicating at least a portion of the additively manufactured orthopaedic prosthetic component so as to loosen the plurality of particles;
    shaking the additively manufactured orthopaedic prosthetic component at a low frequency vibration so as to evacuate the loosened plurality of particles from the additively manufactured orthopaedic prosthetic component;
    filtering the plurality of particles from the fluid by causing the liquid to flow through a filtration substrate and preventing the plurality of particles to flow through the filtration substrate;
    determining a weight of the plurality of particles;
    obtaining a magnified image of at least a portion of the filtration substrate and the plurality of particles supported by the filtration substrate;
    viewing the magnified image on a display;
    surrounding the plurality of particles with at least one boundary line on the image along a respective outer perimeter of the plurality of particles, respectively; and
    determining at least one characteristic of the plurality of particles, the at least one characteristic including at least one of 1) a quantity of groups of the plurality of particles, 2) a size of the plurality of particles, and 3) an aspect ratio of the plurality of particles.

2. The method of claim 1, wherein the loosened plurality of particles is detached from the orthopaedic prosthetic component but disposed in the orthopaedic prosthetic component.

3. The method of claim 1, comprising performing the shaking step while the plurality of particles is submerged in the liquid.

4. The method of claim 1, wherein the sonicating step occurs at a sonication frequency, and the shaking step occurs at a shaking frequency that is less than the sonication frequency.

5. The method of claim 1, wherein the liquid is polar.

6. The method of claim 1, wherein the liquid is substantially nonpolar.

7. The method of claim 1, further comprising the step of increasing a density of the liquid.

8. The method of claim 7, wherein the increasing step comprises adding a salt to the liquid.

9. The method of claim 8, further comprising the step of adding a dispersion agent to the liquid.

10. The method of claim 1, further comprising the step of thresholding the image so as to define the at least one boundary line, wherein an area defined by the boundary represents the plurality of particles.

11. The method of claim 1, wherein the plurality of particles comprises a plurality of groups of particles spaced from each other in their respective entireties, the method further comprising the step of identifying a region of interest on the substrate that surrounds all of the particles prior to the surrounding step.

12. The method of claim 1, further comprising the step of scanning each plurality of particles inside each respective at least one boundary line to determine the characteristic of the plurality of particles.

13. The method of claim 12, further comprising the step of comparing the determined characteristic against a predetermined threshold.

14. The method of claim 1, further comprising the step of placing the filtration substrate under a microscope so as to generate the magnified image.

15. The method of claim 1, further comprising:
    comparing the weight of the plurality of particles to a threshold value; and
    rejecting the additively manufactured orthopaedic prosthetic component if weight of the plurality of particles exceeds the threshold value.

16. The method of claim 1, further comprising weighing the filtration substrate prior to the filtering step,
    wherein the filtering step includes filtering the plurality of particles from the fluid so the plurality of particles is supported by the filtration substrate, and
    wherein determining the weight of the plurality of particles includes weighing the filtration substrate and the plurality of particles.

17. The method of claim 1, wherein the shaking step includes transporting the particles away from the additively manufactured orthopaedic prosthetic component.

18. A method for evaluating an orthopaedic prosthetic component, the method comprising the steps of:
    obtaining a magnified image of at least a portion of a filtration substrate and plurality of particles supported by the filtration substrate, wherein the plurality of particles has been removed from an additively manufactured structure of the orthopaedic prosthetic component;
    viewing the magnified image on a display;
    surrounding the plurality of particles with at least one boundary line on the image along a respective outer perimeter of the plurality of particles, respectively; and
    determining a characteristic of the plurality of particles, the characteristic comprising at least one of 1) a plurality of the plurality of particles that define a quantity of groups of the plurality of particles, 2) a size of the plurality of particles, 3) an aspect ratio of the plurality of particles, and 4) a weight of the plurality of particles.

19. The method of claim 18, further comprising the step of thresholding the image so as to define the at least one boundary line, wherein the boundary line surrounds an area that represents the particle, the method comprising the step of scanning the area so as to determine at least one of 1) a quantity of groups of the plurality of particles, 2) the size of the plurality of particles, and 3) the aspect ratio of the plurality of particles.

20. The method of claim 18, further comprising comparing the characteristic to a threshold value; and
    rejecting the additively manufactured orthopaedic prosthetic component if the characteristic exceeds the threshold value.

* * * * *